(12) United States Patent
Aalders et al.

(10) Patent No.: US 9,029,161 B2
(45) Date of Patent: May 12, 2015

(54) APPARATUS AND METHOD FOR DATING A BODY OR BODY SAMPLE

(75) Inventors: Maurice Aalders, Amsterdam (NL);
Rolf Bremmer, Amsterdam (NL)

(73) Assignee: Academisch Medisch Centrum, Amsterdam (NL)

( * ) Notice: Subject to any disclaimer, the term of this patent is extended or adjusted under 35 U.S.C. 154(b) by 69 days.

(21) Appl. No.: 13/808,249

(22) PCT Filed: Jul. 11, 2011

(86) PCT No.: PCT/EP2011/061785
§ 371 (c)(1),
(2), (4) Date: Apr. 18, 2013

(87) PCT Pub. No.: WO2012/004417
PCT Pub. Date: Jan. 12, 2012

(65) Prior Publication Data
US 2013/0196443 A1    Aug. 1, 2013

(30) Foreign Application Priority Data
Jul. 9, 2010  (GB) .................................. 1011585.5

(51) Int. Cl.
*G01N 33/72*        (2006.01)
*G01N 33/48*        (2006.01)
(Continued)

(52) U.S. Cl.
CPC .............. *G01N 21/25* (2013.01); *G01J 3/0218* (2013.01); *G01J 3/0224* (2013.01); *G01J 3/501* (2013.01); *G01J 3/513* (2013.01); *G01N 21/31* (2013.01);
(Continued)

(58) Field of Classification Search
USPC ........... 436/63, 66, 147, 164, 171; 422/82.05, 422/82.09, 82.12; 435/29; 600/310, 322, 600/476
See application file for complete search history.

(56) References Cited

U.S. PATENT DOCUMENTS

| 5,759,246 A | 6/1998 | Frey et al. |
| 8,750,952 B2 * | 6/2014 | Aalders .......................... 600/310 |
| 2011/0112385 A1 | 5/2011 | Aalders |

FOREIGN PATENT DOCUMENTS

WO        2009/130580        10/2009

OTHER PUBLICATIONS

Hanson, et al., "A Blue Spectral Shift of the Hemoglobin Soret Band Correlates with the Age (Time Since Deposition) of Dried Bloodstains," PLoS ONE, Sep. 2010, vol. 5, Issue 9.
(Continued)

*Primary Examiner* — Maureen Wallenhorst
(74) *Attorney, Agent, or Firm* — Miles & Stockbridge P.C.

(57) ABSTRACT

A method and apparatus for dating a body sample, such as blood, includes taking at least one spectroscopic measurement of the sample at at least two predetermined positions in the spectrum having spectral characteristics corresponding to at least two predetermined substances present in the sample that have a time varying relationship with each other. A measured relative concentration of each of the predetermined substances is then determined from the measurement, and the measured relative concentrations of the two predetermined substances is compared with a known variation of the relative concentrations of the two predetermined substances over time. A good fit of the measured relative concentrations to the known variation of the relative concentrations is then determined, so as to provide an indication of the age of the sample. Alternatively, instead of measuring the relative concentrations of each of the predetermined substances, the rate of change of the relative concentrations is determined.

22 Claims, 13 Drawing Sheets

(51) Int. Cl.
  G01N 21/25    (2006.01)
  G01J 3/02     (2006.01)
  G01J 3/50     (2006.01)
  G01J 3/51     (2006.01)
  G01N 21/31    (2006.01)
  G01N 21/47    (2006.01)
(52) U.S. Cl.
  CPC ...... G01N 21/474 (2013.01); *G01N 2201/0826* (2013.01); *G01N 2201/0833* (2013.01)

(56) References Cited

OTHER PUBLICATIONS

Strasser, et al. "Age determination of blood spots in forensic medicine by force spectroscopy," (abstract), Forensic Scienc International 170 (2007).

Blazek, et al., "Spectroscopic Age Determination of Blood Stains: New Technical Aspects," Acta Med Leg Soc (Liege) 32 (1982), pp. 613-616.

Kohler, et al., "On the Suitability of Spectrophotometric Analyses for the Estimation of Blood Stain Age," Z. Rechtsmedizin 79, pp. 183-187 (1977).

Kind et al.; "Estimation of Age of Dried Blood Stains by a Spectrophotometric Method"; Forensic Science; Elsevier; vol. 1, No. 1; Apr. 1, 1972; pp. 27-54.

Fujita et al.; "Estimation of the Age of Human Bloodstains by Electron Paramagnetic Resonance Spectroscopy: Long-Term Controlled Experiment on the Effects of Environmental Factors"; Forensic Science International, Elsevier Scientific Publishers Ireland Ltd, IE, vol. 152, No. 1; Aug. 11, 2005; No. 1; pp. 39-43.

Henszge et al.; "Estimation of the Time Since Death in the Early Post-Mortem Period"; Forensic Science International, Elsevier Scientific Publishers Ireland Ltd, IE, vol. 144, No. 2-3, Sep. 10, 2004; pp. 167-175.

Jack Ballantyne: "Determination of the Age (Time Since Deposition) of a Biological Stain"; Aug. 1, 2008; pp. 1-84; XP55007873; Figures 2-5, 9-11; pp. 33-44.

International Search Report based on PCT/EP2011/061785 mailed Oct. 6, 2011.

* cited by examiner $$I_{blood} = \underbrace{\underbrace{I_0 e^{-\mu_{a,bl}(\lambda) \cdot d_{bl}}}_{I_1} \cdot e^{-\mu_{a,host}(\lambda) \cdot d_{host}} \cdot e^{-\mu_{a,bl}(\lambda) \cdot d_{bl}}}_{I_{blood}}$$

| Environment | Temperature°C | Humidity % | A | B |
|---|---|---|---|---|
| Outside Winter Night | -20 | 40 | 0.0451 | 3.5101 |
| Outside Summer Night | 4 | 40 | 0.0498 | 3.8507 |
| Air-conditioned Inside Office | 23 | 40 | 0.0632 | 10.8621 |
| Outside Summer Day in Sun | 36 | 40 | 0.0820 | 16.237 |

APPARATUS AND METHOD FOR DATING A BODY OR BODY SAMPLE

CROSS REFERENCE TO RELATED APPLICATIONS

This application is a §371 National Stage Application of PCT/EP2011/061785 filed Jul. 11, 2011, which claims priority to United Kingdom Application No. 1011585.5 filed Jul. 9, 2010.

BACKGROUND OF THE INVENTION

1. Field of the Invention

The present invention relates to an apparatus and method for dating a body or body sample, preferably, but not exclusively, a sample of a body fluid, such as blood, which is external to the body, for example, having caused stains on an external substrate, such as a floor, wall, and clothing.

2. Description of Related Art

It is well known that dating of external blood stains is a useful forensic technique to determine when a particular injury was caused to a person. Thus, the injury may have been such that the skin was punctured and blood was spilt. Alternatively, traces of other bodily fluids, such as saliva may be found. In both cases, however, there is a need to accurately determine the age of the stain or sample, so as to determine when the body fluid was released from the body.

In general, determination of the age of external blood stains has been carried out by a variety of methods. Although, historically, this was carried out by very roughly estimating the age based on the colour of the blood stain, more "scientific" methods have recently been employed. Most such methods rely on the fact that, when blood leaves the human body, haemoglobin in the blood is oxidised to met-haemoglobin. Various methods have therefore tried to use different characteristics of haemoglobin and met-haemoglobin to try to determine their relative concentrations and, from those, to try to determine the age of the blood stain. However, some of these methods require very complicated and advanced technical equipment, so that they cannot easily be done at the scene of the injury, for example a crime scene. In other cases, known techniques often compromise the blood traces by using chemicals or by requiring that the stains be taken to a laboratory in order to properly analyse them. Still others of the methods have proved not to be reliable since they provide too high a deviation compared to the actual age of the stains. One recent new technique that has been suggested is to use atomic force microscopy for high-resolution imaging of erythrocytes in a blood sample to detect elasticity changes on a nanometer scale (see the paper "Age determination of blood spots in forensic medicine by force spectroscopy" by Stefan Strasser, Albert Zink, Gerald Kada, Peter Hinterdorfer, Oliver Peschel, Wolfgang M. Heckl, Andreas G. Nerlich and Stefan Thalhammer published in Forensic Science International, Volume 170, Issue 1, 20 Jul. 2007, Pages 8-14).

In PCT Patent Application No. WO 2009/130580 there is described a technique for dating blood samples by taking a series of spectroscopic measurements of the sample to determine the concentrations of oxy-haemoglobin and met-haemoglobin at several spaced points in time. The ratios of the concentrations at the different points in time are then analysed to estimate when their concentrations were at a limit of their concentrations, thereby providing an indication of the age of the blood sample.

Although the above method is an improvement on the previous techniques, the estimate is based on the assumption that the reaction rate prior to the first measurement being made is the same (or at least roughly the same over the period) as the reaction rate over the time when the measurements are taken. Since it requires a series of measurements to be made, it can take some time for the estimate of the age of the sample to be determined. More accurate methods are therefore, of course, desirable.

Apart from body samples, it will be apparent that the assumption that the reaction rate prior to the first measurement being made is the same as the reaction rate when the measurements are taken also applies to other methods of dating of both body samples, and, in some cases, to methods of dating bodies, for example by taking the temperature of a body either once or several times and then assuming that it is cooling at a particular rate. However, such methods can be inaccurate because the cooling rate may depend on environmental factors.

SUMMARY

The present invention therefore seeks to provide an apparatus and method for dating a body sample, which overcomes, or at least reduces the above-mentioned problems of the prior art.

Accordingly, in a first aspect, the invention provides a method of dating a body sample comprising taking at least one spectroscopic measurement of the sample, the measurement including at least two predetermined positions in the spectrum, the positions having spectral characteristics corresponding to at least two predetermined substances present in the sample that have a time varying relationship with each other, determining a measured relative concentration of each of the predetermined substances present in the sample from the spectroscopic measurement, comparing the measured relative concentrations of the at least two predetermined substances with a known variation of the relative concentrations of the at least two predetermined substances over time, and determining a good fit of the measured relative concentrations to the known variation of the relative concentrations, so as to provide an indication of the age of the sample.

According to a second aspect, the invention provides a method of dating a body sample, comprising taking at least two spectroscopic measurements of the sample at different times, the measurements including at least two predetermined positions in the spectrum, the positions having spectral characteristics corresponding to at least two predetermined substances present in the sample that have a time varying relationship with each other, determining a measurement of change in the relative concentration of each of the predetermined substances present in the sample from the spectroscopic measurements, comparing the measurements of change in the relative concentration of each of the predetermined substances with a known variation of the changes in the relative concentrations of the predetermined substances over time, and determining a good fit of the measurements of changes in the relative concentration to the known variation of the changes in the relative concentrations, so as to provide an indication of the age of the sample.

In a preferred embodiment, both methods can be used, if appropriate, for example, if the changes in the relative concentrations of each of the predetermined substances are small.

In one embodiment, the sample is a body fluid, which may be blood.

Preferably, the predetermined substances comprise two or more of oxy-haemoglobin, met-haemoglobin and haemichrome.

The measurement(s) preferably includes at least three predetermined positions in the spectrum, the positions having spectral characteristics corresponding to at least three predetermined substances, the three predetermined substances comprising oxy-haemoglobin, met-haemoglobin and haemichrome.

Preferably, the spectroscopic measurement(s) comprise reflectance, Raman or fluorescence spectroscopic measurement(s).

According to a third aspect, the invention provides a method of dating a body or body sample, the method comprising measuring one or more time-varying parameters of the body or body sample, the time-varying parameter(s) having a rate of time variance that changes according to at least one environmental factor, providing a database of rates of time variance of the time-varying parameter(s) for the at least one environmental factor, estimating the at least one environmental factor for the particular environment(s) where the body or body sample was located prior to the at least one measurement being made, and determining an estimate of the age of the body or body sample by utilising the at least one measurement of the or each time-varying parameter and the rate of time variance for that time-varying parameter for the estimated at least one environmental factor.

In one embodiment, the time-varying parameter comprises temperature.

Preferably, the time-varying parameter(s) comprises two or more of:
  concentration of oxy-haemoglobin;
  concentration of met-haemoglobin; and
  concentration of haemichrome.

The environmental factor preferably comprise one or more taken from:
  ambient temperature;
  ambient humidity;
  thermal conductivity of a substrate on which the body or body sample is located; and
  absorption by a substrate on which the body or body sample is located.

According to a further aspect, the invention provides an apparatus for dating a body sample comprising a device for taking at least one spectroscopic measurement of the sample, the measurement including at least two predetermined positions in the spectrum, the positions having spectral characteristics corresponding to at least two predetermined substances present in the sample that have a time varying relationship with each other, and a processing device for determining a measured relative concentration of each of the predetermined substances present in the sample from the spectroscopic measurement, comparing the measured relative concentrations of the at least two predetermined substances with a known variation of the relative concentrations of the at least two predetermined substances over time, and determining a good fit of the measured relative concentrations to the known variation of the relative concentrations so as to provide an indication of the age of the sample.

According to still further aspect, the invention provides an apparatus for dating a body sample comprising a device for taking at least two spectroscopic measurements of the sample at different times, the measurements including at least two predetermined positions in the spectrum, the positions having spectral characteristics corresponding to at least two predetermined substances present in the sample that have a time varying relationship with each other, and a processing device for determining a measurement of change in the relative concentration of each of the predetermined substances present in the sample from the spectroscopic measurements, comparing the measurements of change in the relative concentration of each of the predetermined substances with a known variation of the changes in the relative concentrations of the predetermined substances over time, and determining a good fit of the measurements of changes in the relative concentration to the known variation of the changes in the relative concentrations so as to provide an indication of the age of the sample.

In a preferred embodiment, if the changes in the relative concentrations of each of the predetermined substances are small, the processing device further determining a measured relative concentration of each of the predetermined substances present in the sample from the spectroscopic measurement, comparing the measured relative concentrations of the at least two predetermined substances with a known variation of the relative concentrations of the at least two predetermined substances over time, and determining a good fit of the measured relative concentrations to the known variation of the relative concentrations so as to provide an indication of the age of the sample.

In one embodiment, the sample is a body fluid, which may be blood.

Preferably, the predetermined substances comprise two or more of oxy-haemoglobin, met-haemoglobin and haemichrome.

The measurement(s) preferably includes at least three predetermined positions in the spectrum, the positions having spectral characteristics corresponding to at least three predetermined substances, the three predetermined substances comprising oxy-haemoglobin, met-haemoglobin and haemichrome.

Preferably, the spectroscopic measurement(s) comprise reflectance, Raman or fluorescence spectroscopic measurement(s).

More preferably, the reflectance spectroscopic measurements include near infra-red wavelength radiation of above 850 nm or even more preferably between 1150 nm and 2500 nm.

In a further aspect, the invention provides an apparatus for dating a body or body sample, comprising a device for taking at least one measurement of one or more time-varying parameters of the body or body sample, the time-varying parameter(s) having a rate of time variance that changes according to at least one environmental factor; and a processing device for obtaining rates of time variance of the time-varying parameter(s) for the at least one environmental factor, for the particular environment(s) where the body or body sample was located prior to the at least one measurement being made, from a database of different rates of time variance of the time-varying parameter(s) for different environments, and determining an estimate of the age of the body or body sample by utilising the at least one measurement of the or each time-varying parameter and the rate of time variance for that time-varying parameter.

In one embodiment, the time-varying parameter comprises temperature.

Preferably, the time-varying parameter(s) comprises two or more of:
  concentration of oxy-haemoglobin;
  concentration of met-haemoglobin; and
  concentration of haemichrome.

The environmental factor preferably comprises one or more taken from:
  ambient temperature;
  ambient humidity;
  thermal conductivity of a substrate on which the body or body sample is located; and absorption by a substrate on which the body or body sample is located.

BRIEF DESCRIPTION OF THE DRAWINGS

Several embodiments of the invention will now be more fully described, by way of example, with reference to the drawings, of which.

DETAILED DESCRIPTION OF PREFERRED EMBODIMENT

Figure 1:
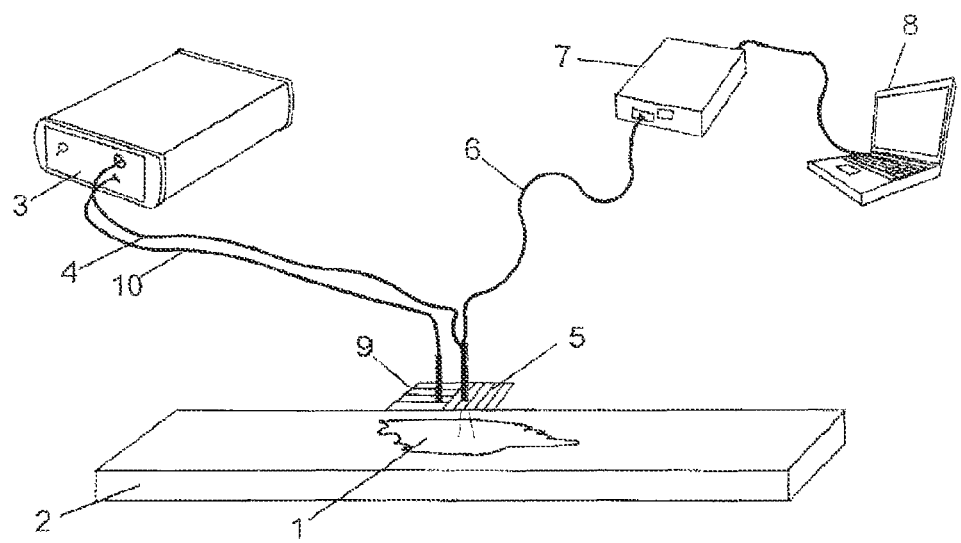
FIG. 1 is a schematic diagram of an apparatus constituting a first embodiment of the invention.

Referring first to FIG. 1, there is shown a schematic apparatus for measuring the age of bloodstains on a substrate. As shown, the bloodstain 1 is present on a host material 2. The bloodstain 1 is illuminated by light from a light source 3 via a first optical fibre 4. The light is directed onto the bloodstain from the end of the first optical fibre 4 via a linear polarizer 5. A second optical fibre 6 is arranged next to first optical fibre 4 to detect light that is reflected from the bloodstain 1 and which passes back through the linear polarizer 5. Such reflected light is, of course, low-order scattered, since its polarization has not been substantially changed. This low-order scattered reflected light is then transmitted via the second optical fibre 6 to a spectrograph 7. The results of the spectrograph, which will be further explained below, are then passed to a computer 8 for processing. A cross polarizer 9 is provided next to the linear polarizer and a third optical fibre 10 is arranged to detect light reflected from the bloodstain 1 that passes through the cross polarizer. This reflected light will be high-order scattered light and this light is transferred via the third optical fibre 10 to a second channel of the spectrograph. This light will contain information of the host material, later to be used for correction. Low-order scattered light comes from the top of the blood and high-order from the bottom (or from the host material).

Figure 2:
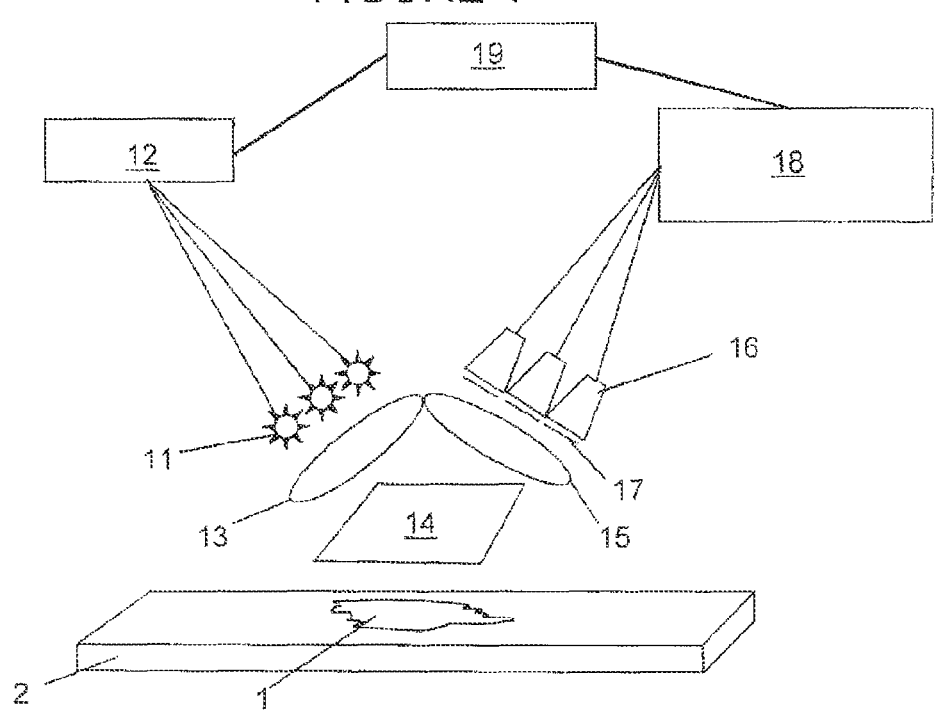
FIG. 2 is a schematic diagram of an apparatus constituting a second embodiment of the invention.

FIG. 2 shows a second embodiment of similar apparatus to that of FIG. 1, but with different forms of the same basic elements. Thus, in this case, the bloodstain 1 is again on the host material 2, but this time it is illuminated by light produced by several Light Emitting Diodes (LEDs) 11 controlled and driven from an LED driver 12. The LEDs 11 are different, so that each emits light of a different wavelength or waveband from that of the other LEDs 11. The light from the LEDs 11 illuminates the bloodstain 1 via a first lens 13 and a linear polarizer 14. In this case, a second lens 15 directs the light reflected from the bloodstain and transmitted back through the linear polarizer 14, i.e. the low-scattered light, to several photo detectors 16, each of which has a different filter 17 between it and the second lens 15, so that each photodetector 16 detects reflected light of a different wavelength or waveband from that of the other photodetectors 16. The filters 17 are matched to transmit light of the wavelengths or wavebands that are emitted by the LEDs 11. The outputs from the photodetectors 16 are passed to a signal processing unit 18, which is coupled to a computer 19. The computer 19 is also used to control the LED driver 12. This implementation can be easily designed into a hand held measurement device, to enable ease of use at, for example, a crime scene. Again, low-order scattered light comes from the top of the blood.

Figure 3:
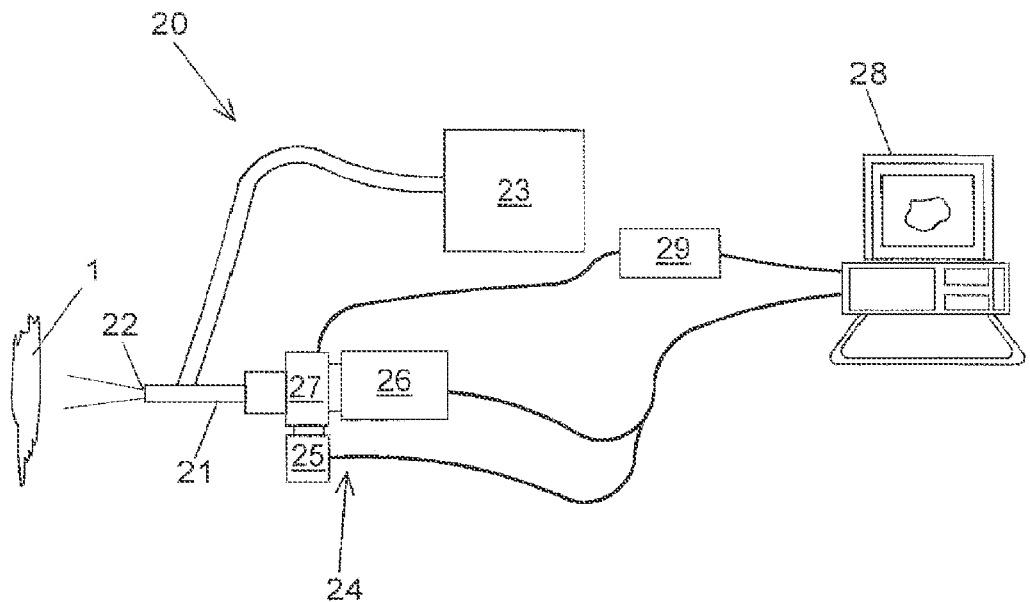
FIG. 3 is a schematic diagram of an apparatus constituting a third embodiment of the invention.

FIG. 3 shows a third embodiment of the apparatus. In this case, the bloodstain 1 is illustrated as being in a vertical plane, for example on a wall. In this case, a hand-held apparatus 20 includes a light guide 21 having an appropriate optical system at an end 22 thereof for transmitting illuminating light from an input light module 23 through the optical system and out onto the bloodstain. Reflected light is then detected through the optical system and transmitted through the light guide 21 to a Spectral Imaging Camera 24. The Spectral Imaging Camera 24 includes both a colour camera 25 and an intensified camera 26. The detected light from the bloodstain 1 transmitted through the light guide 21 passes through a Liquid Crystal Tunable Filter (LCTF) 27 from where it is directed to either the colour camera 25 or the intensified camera 26 (or both). The LCTF operates as a tunable band pass filter, the centre wavelength of which can be rapidly tuned across a wide spectral range. The Spectral Imaging Camera 24 is coupled to a computer 28, which both receives the output data from the Spectral Imaging Camera 24 for analysis and controls the Spectral Imaging Camera 24, including the colour camera 25, the intensified camera 26, and the LCTF 27 via LCTF control electronics 29. Advantages of the LCTF, apart from electronic tuning, include high spectral resolution, simple to integrate in imaging systems and fast response time. Any filtering wavelength in the range from 400 to 720 nm can be rapidly selected either by random access or sequential tuning which, in the last case, yields a full reflection spectrum for every pixel on the CCD (=every position on the tissue). In addition, both filtered (spectral) and unfiltered (white light) images are available to facilitate the direct association of spectroscopic features with specific anatomical sites.

The most direct mode of spectral imaging is to illuminate the target area while acquiring a series of images assessing the remittance spectrum of every pixel. This data set is called a 'spectral cube', containing information about the absorbers in the tissue which allows determining relative concentrations of the absorbers. One such LCTF is manufactured by Cri (UK) and has an active diameter of 20 or 35 mm, a tuning range from 400 to 720 nm (which means that a separate detector is required for measuring water absorption), a throughput of less than 50% and a filtering bandwidth of nominally 7 nm (collimated light).

However, it will be appreciated that other filters can be used depending on the application and the accuracy of the results required. Thus, for example, an Acousto-Optical tuneable filter (AOTF), could be used instead of the LCTF. In any event, both types of filter produce data in the form of a spectral cube, which contains information about the absorbers in the tissue which can be used to determine relative concentrations of the chromophores. The reflected light at each position will be used to calculate the corresponding absorption spectrum at each pixel or group of pixels. This will provide the position dependent concentrations of the chromophores.

Inside a healthy human body, haemoglobin molecules are mainly present in two forms: one without oxygen: de-oxy-haemoglobin (Hb) and one saturated with oxygen: oxy-haemoglobin ($HbO_2$). The average saturation level of arterial blood is >90% and of venous blood is >70%. In addition, only a small part (~1%) of $HbO_2$ is auto-oxidized into a third form, met-haemoglobin (met-Hb). Reductase protein cytochrome b5 will then reduce met-Hb back to Hb.

Figure 5:
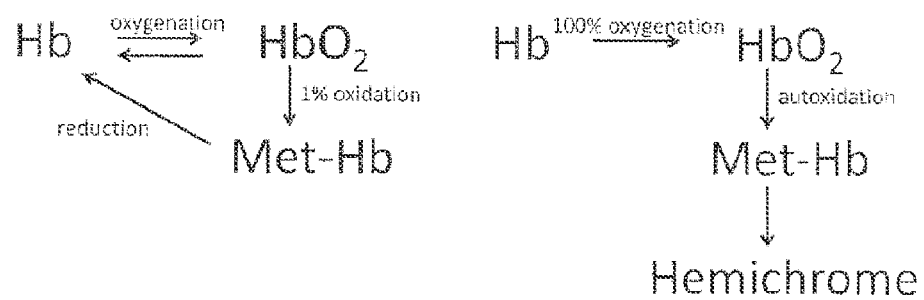
FIG. 5 is a schematic representation of haemoglobin kinetics both inside the body and external to the body.

It has been found, however, that outside the body, blood will first totally saturate to $HbO_2$ as soon as it comes in contact with the oxygen in the atmosphere. This autoxidation process will continue and due to a decreasing availability of cytochrome b5, necessary for reduction of met-Hb, the transition of $HbO_2$ into met-Hb will become irreversible. Once the haemoglobin molecules are autooxidized to met-Hb they will denature to haemichrome (HC). HC is formed through changes of protein conformation so that atoms endogenous to the protein become bound to the iron at the sixth ligand. A schematic overview of the haemoglobin kinetics, of both in-vivo and extracorporeal blood is shown in FIG. 5.

Figure 4:
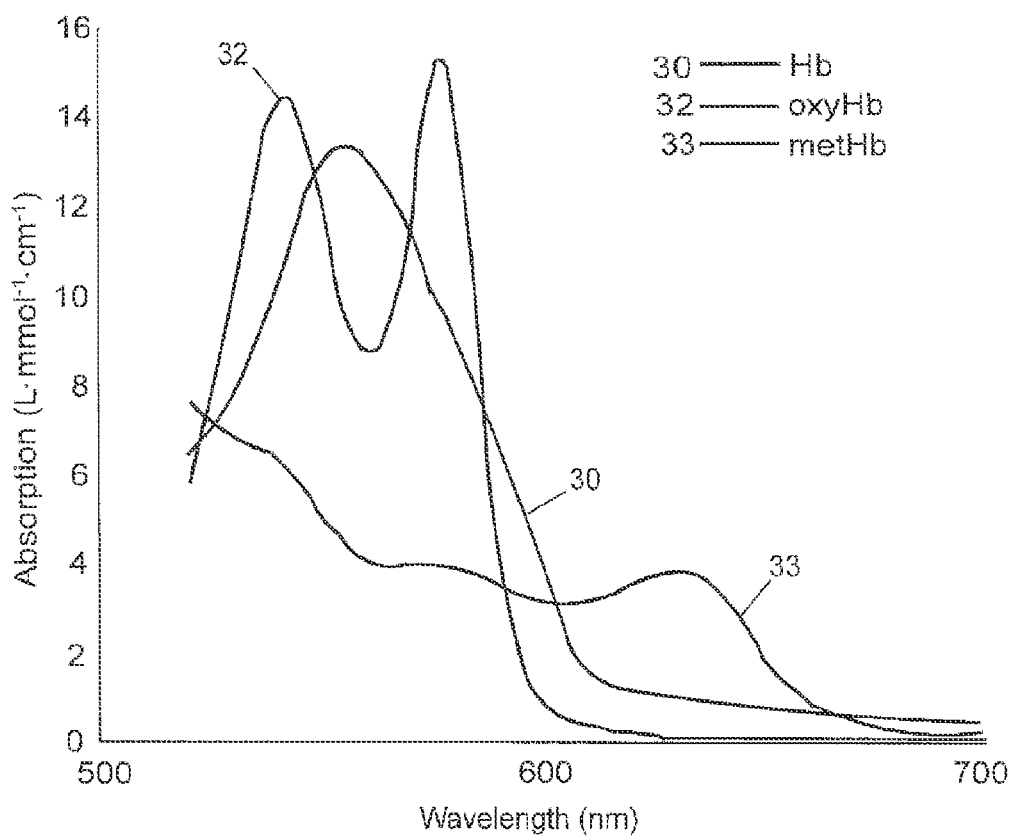
FIG. 4 shows absorption spectra for haemoglobin (Hb), met-haemoglobin (metHb) and oxy-haemoglobin ($HbO_2$)
Figure 6:
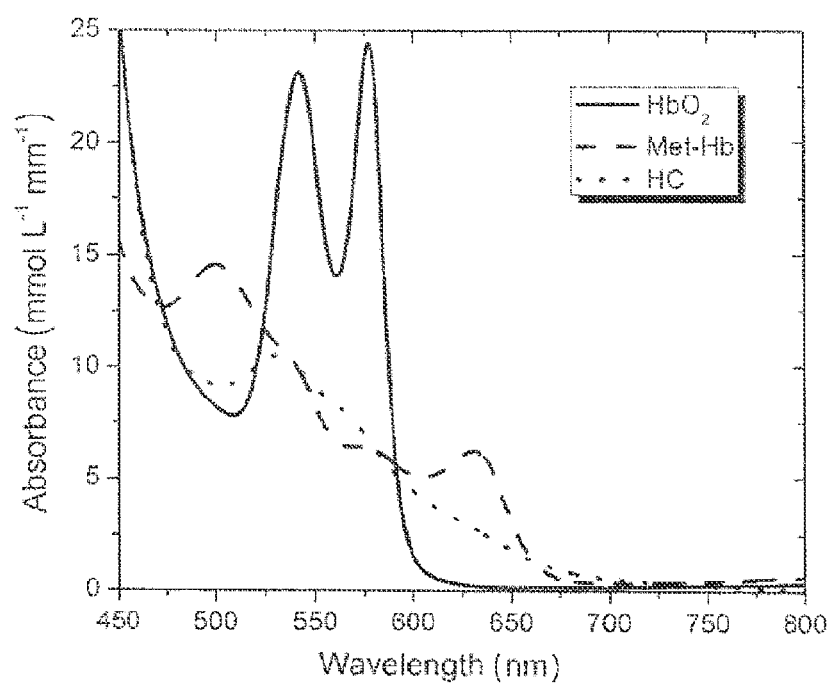
FIG. 6 shows absorption spectra for met-haemoglobin, oxy-haemoglobin and haemichrome (HC)

FIG. 4 shows absorption spectra for haemoglobin (30), met-haemoglobin (31) and oxy-haemoglobin (32). It will be seen that haemoglobin has an absorption peak at 556 nm, oxy-haemoglobin has a pair of peaks at 542 and 578 nm, and met-haemoglobin has a peak at 630 nm. FIG. 6 shows the absorption spectra for $HbO_2$, met-Hb, and HC. It will be seen that they differ at over 450-800 nm. Thus, by using Diffuse Reflectance Spectroscopy at these wavelengths to monitor this chemical process in bloodstains, a more accurate determination of the age of the bloodstain can be determined.

It will thus be seen that by using that by measuring the detected light, one can determine the (relative) quantities of the contents of the measured volume. From the total reflectance spectrum for the bloodstain, for the host material, for example coloured cloth, and a reference spectrum for the light source, one can correct for the properties of the light source and obtain the corrected reflectance of the bloodstain. From these spectra, the relative concentrations of the chosen substances in the bloodstain can be determined.

Figure 7:
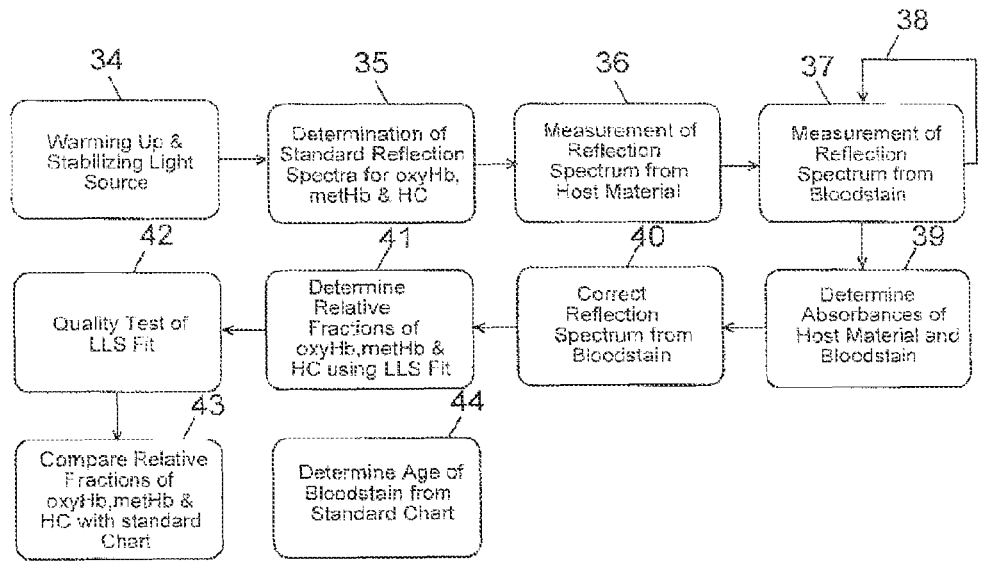
FIG. 7 is a schematic flowchart of a first process for determining the time at which blood was first exposed to air.

Thus, the process of determining the relative quantities of oxy-haemoglobin, met-haemoglobin, haemichrome and water in order to calculate the moment of deposition of extracorporeal blood is based on a spectroscopic measurement technique which only measures the low order scattered light and fits the resulting data using a procedure that allows for the elimination of background artefacts and scaling of the absorption curves. The process is shown generally in FIG. 7.

As can be seen, the process starts by warming up and stabilising the light source 34. The time at which a stable output is reached depends on the type of light source. A halogen lamp requires 10-30 minutes, but LEDs can be used much sooner, although they have to be kept at a constant temperature. Once the light source is stabilised, in order to be able to correct for the spectrum of the particular light source being used, a reference spectrum is measured (35) using a neutral reflector, such as a spectralon. In this case, the light from the light source is made incident onto the spectralon and the reflected light is passed to the detector using the same light path, for example optical fibres if they are being used, so that a spectrum including the light source, the light paths and the detector characteristics can be obtained as a reference. Next, the reflection spectrum from the host material is obtained (36). Clearly, this will bear the characteristics of the reference spectrum plus the absorption and reflection characteristics of the host material. After these two references are obtained, measurement on the bloodstain is commenced (37). If desired, one or more reflectance spectra may be measured at different positions on the bloodstain (38).

In essence, the absorbance of the host material and of the bloodstain can be found from:

$$\text{Absorbance hostmaterial} = \ln\left(\frac{\text{refl. hostmaterial}}{\text{refl. reference}}\right)$$

$$\text{Absorbance bloodstain} = \ln\left(\frac{\text{refl. bloodstain}}{\text{refl. reference}}\right)$$

From the measurements of the spectra, the absorbances of the host material and the bloodstain can be calculated (39).

Figure 8:
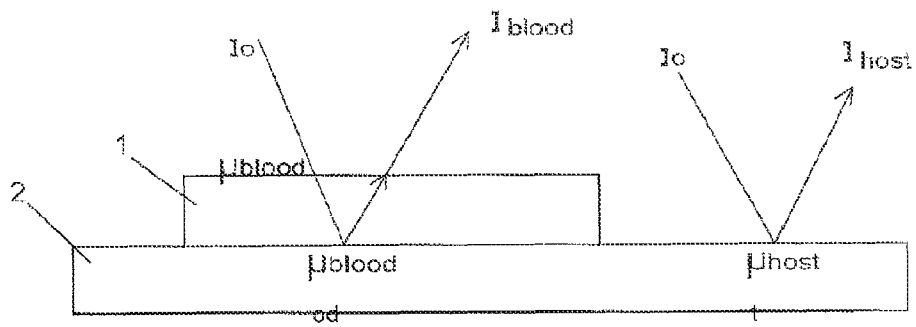
FIG. 8 is a schematic diagram of the geometry of a simple model of light reflectance from two layers.

This is illustrated schematically in FIG. 8, where the geometry of the situation, is shown in simplified form considering a simple model of two layers, being the blood stain 1 and the host material 2. As will be apparent, the intensity of the light detected at the detector $I_{blood}$, whether it be the spectrograph 7, the photodetector 16 or the Spectral Imaging Camera 24, at a particular wavelength, will depend on the intensity of the incident light $I_0$ directed onto the bloodstain and will depend on the amount of light reflected by the bloodstain, reflected by the host material and then transmitted by the bloodstain. This can be expressed, simply as:

$$I_{blood} = I_0 e^{-\mu_{a,bl}(\lambda) \cdot d_{bl}} \cdot e^{-\mu_{a,host}(\lambda) \cdot d_{host}} \cdot e^{-\mu_{a,bl}(\lambda) \cdot d_{bl}}$$

where
$I_{blood}$ is the intensity of the received light;
$I_0$ is the intensity of the incident light;
$\mu_{a,host}(\lambda)$ is the absorption coefficient of the host material (in $mm^{-1}$) at wavelength $\lambda$; and
$\mu_{a,bl}(\lambda)$ is the absorption coefficient of the bloodstain (in $mm^{-1}$) at wavelength $\lambda$;
$d_{host}$ is the optical pathlength through the host (in mm); and
$d_{bl}$ is the optical pathlength through the bloodstain (in mm).

Once the absorbance spectra of the bloodstain and the host material are determined, they can be used, together with the known spectra of blood, oxy-haemoglobin, met-haemoglobin and water as the input matrix for the fitting procedure to determine the relative concentrations of met-haemoglobin and oxy-haemoglobin in the bloodstain (40). This process is based on the Kubelka Munk Reflection Theory, which is a simplified solution of the radiation transport equation. This theory is employed to analyze the recorded diffuse reflectance spectra. The following formula was used:

$$\frac{I}{I_0} = 1 - \frac{K}{S}\left(\sqrt{1 + \frac{2S}{K}} - 1\right) \quad (1)$$

Here I denotes the bloodstain's reflectance, and $I_0$ is the reflectance of the substrate surface. K and S represent the absorption and scattering of the bloodstain. Here $K=\mu_a/\eta$ with $\mu_a$ the absorption coefficient per unit length which depends on wavelength and $\eta$ being a dimensionless function depending on albedo. For scattering S, Lorentz-Mie scattering was assumed:

$$S = S_0 \cdot \left(\frac{\lambda}{\lambda_0}\right)^{-0.4} \quad (2)$$

The scattering S depends on the wavelength $\lambda$ in nm, $\lambda_0$ is 450 nm and the scattering coefficient at 450 nm, $S_0$ is 13.5 mm$^{-1}$. The scattering was set to be constant over the total measured time period.

Then, the known spectra of oxy-haemoglobin, met-haemoglobin and haemichrome are fitted (41) using a linear constrained optimisation fitting algorithm to the corrected spectra for oxy-haemoglobin, met-haemoglobin and haemichrome. In this case a linear least squares (LLS) fit was used. The LLS fitting algorithm varies the amplitudes of the three absorption spectra, in order to find the combination of the three with a minimum of difference between the theory and the diffuse reflectance spectrum. The LLS fitting procedure yields the estimated haemoglobin fractions of $HbO_2$, met-Hb and HC.

Figure 9:
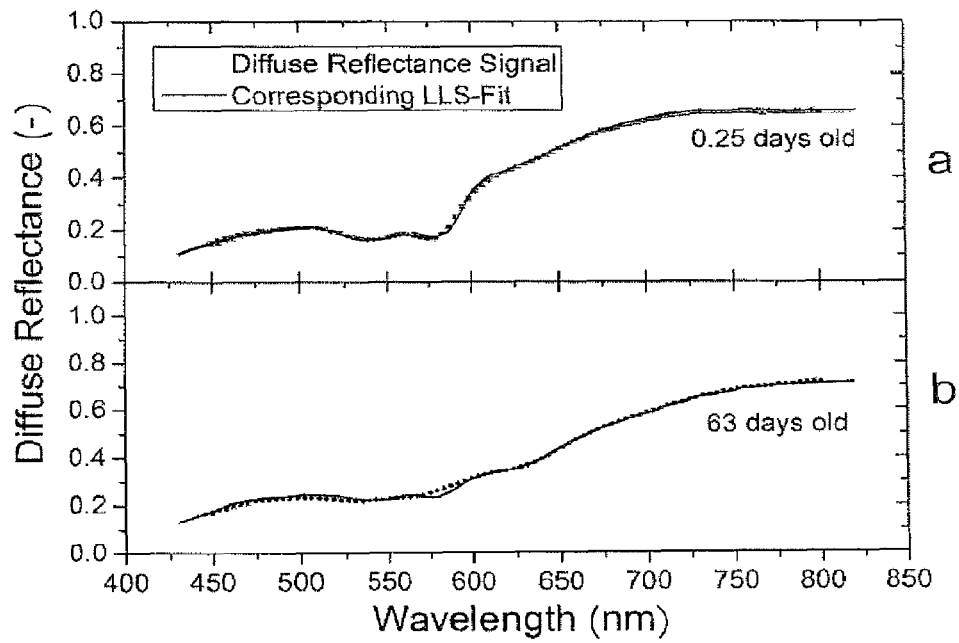
FIGS. 9a and 9b are schematic graphs showing the linear fit of the three components on a measured diffuse reflectance signal for a bloodstain that is ¼ and 63 days old, respectively.

For correct data analysis, it is important that there is a high correlation between the reflectance signal and the LLS fit. If the correlation is poor, over compensation by one of the compounds may occur, and the outcome of the fitting procedure becomes unreliable. To prevent this, a quality test between data and fit is utilized (42). Thus, only LLS fits with correlation coefficient $R^2>0.98$ were accepted. Two typical diffuse reflectance spectra with corresponding LLS fits are shown in FIG. 9, where FIG. 9(*a*) shows a spectrum for a bloodstain that is ¼ day old and FIG. 9(*b*) shows a spectrum for a bloodstain that is 63 days old. As can be seen the LLS fit is fairly accurate in both cases. Measurements may also be carried out at different positions on the bloodstain to see whether the bloodstain is homogeneous, or whether there is a variation within a stain and what the variation is.

Figure 10A:
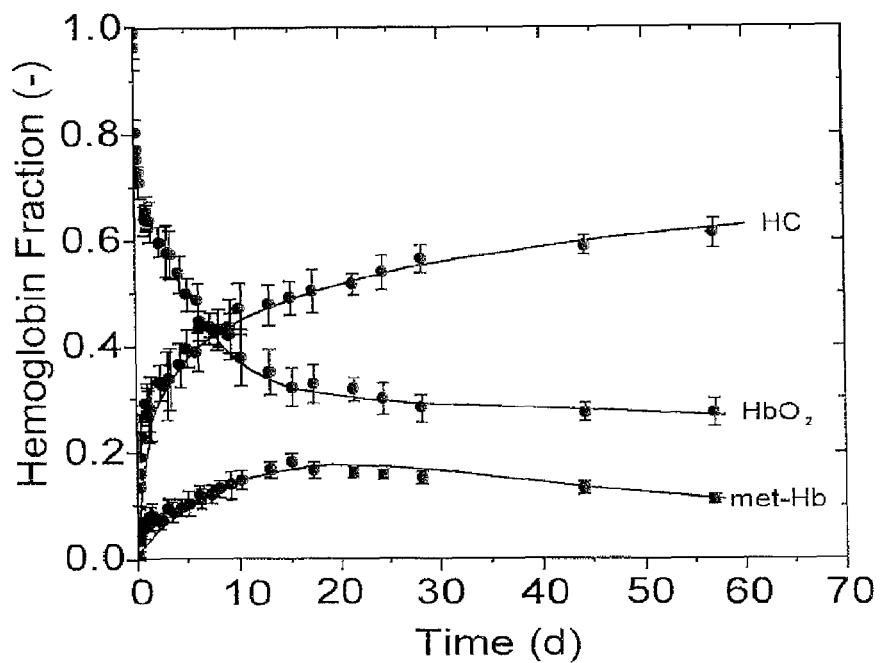
FIG. 10a is a graph showing the relative concentrations of $HbO_2$, metHb and HC in a bloodstain over time up to around 60 days.
Figure 10B:
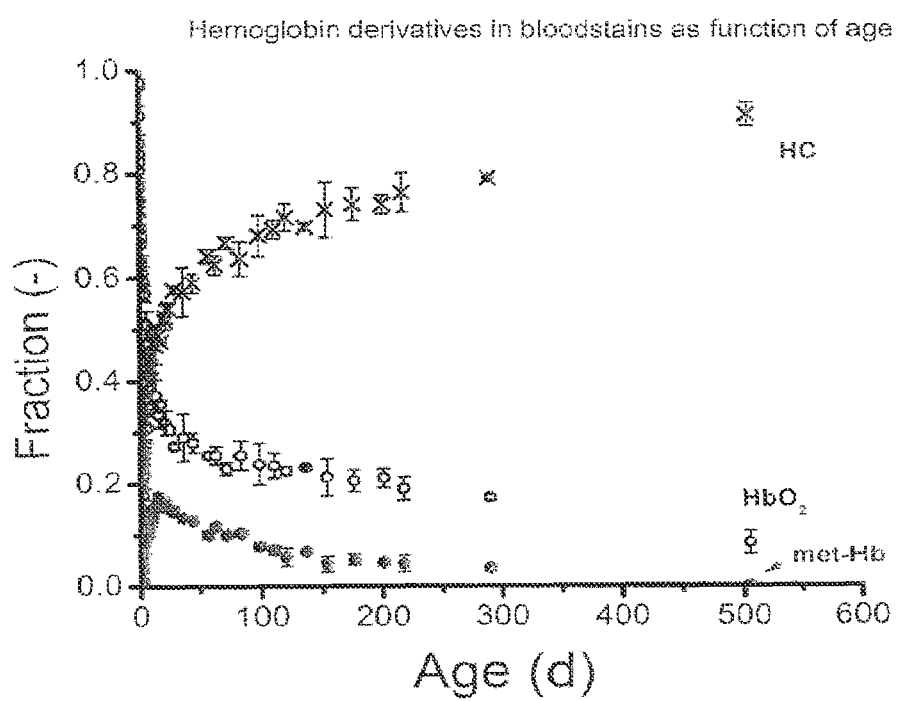
FIG. 10b is a graph showing the relative concentrations of $HbO_2$, metHb and HC in a bloodstain over time up to around 500 days.

FIGS. 10*a* and 10*b* show that the amount of $HbO_2$ decreases over time, because of the oxidation into met-Hb. FIG. 10*a* comprises data up to around 60 days whereas FIG. 10*b* comprises data up to around 500 days. It appears that the amount of met-Hb reaches a maximum after two weeks; met-Hb, in its turn, denatures into HC. At all moments, a unique combination of these three haemoglobin compounds exists, which can be utilized for adequate age determination. For performing age estimation, the haemoglobin fractions determined from the validation set are matched (43) with the comparison ("standard") graph in FIG. 10*a* or 10*b*. This can be done by eye or by an appropriate matching algorithm. The relative differences between the measured $HbO_2$, met-Hb and HC fractions on one hand and the values in the "standard" graph are calculated and the best match is determined. The best match can be considered to be found at a minimum difference of this sum. This thus provides the estimated age of the bloodstain (44). Alternatively, each component can be matched to the comparison graph and the age determined. The ages so determined can then be averages to provide an age estimation. Other techniques of making the age estimation based on a comparison of the measured $HbO_2$, met-Hb and HC fractions on one hand and the values in the "standard" graph can be used, as will be well known to a person skilled in the art.

Figure 11:
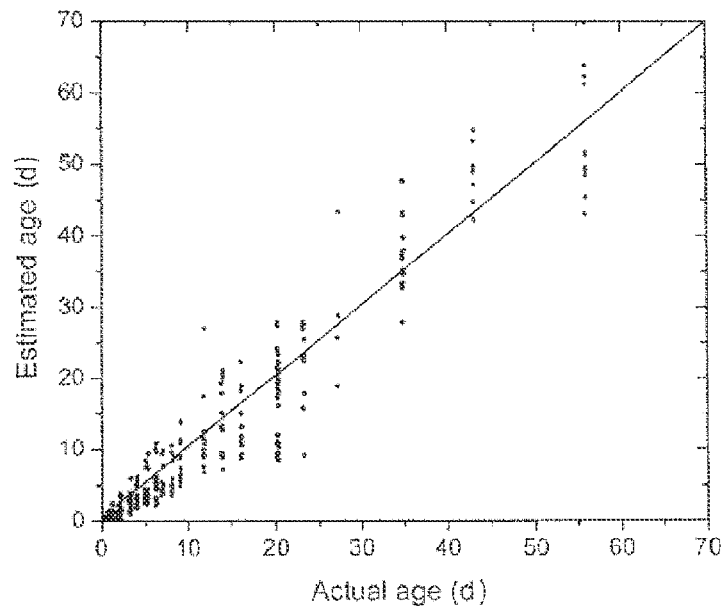
FIG. 11 is a graph showing the age estimation for test samples to compare the estimated age with the known actual age.

FIG. 11 shows the age estimation following the above described procedure for test samples where the age of the bloodstains was known to compare the estimated age with the known actual age. The combination of biological variation and uncertainties in the measurement procedure cause the spreading of the age estimation. For instance, at an age of seven days, the estimated age varies between four and ten days (±50). When measured at 55 days, the estimated age varies between 45 and 70 days (±25% r).

It will, of course, be appreciated that although the technique described above used reflectance spectroscopy, any appropriate type of spectroscopy, such as Raman or reflectance spectroscopy could be used.

Figure 12:
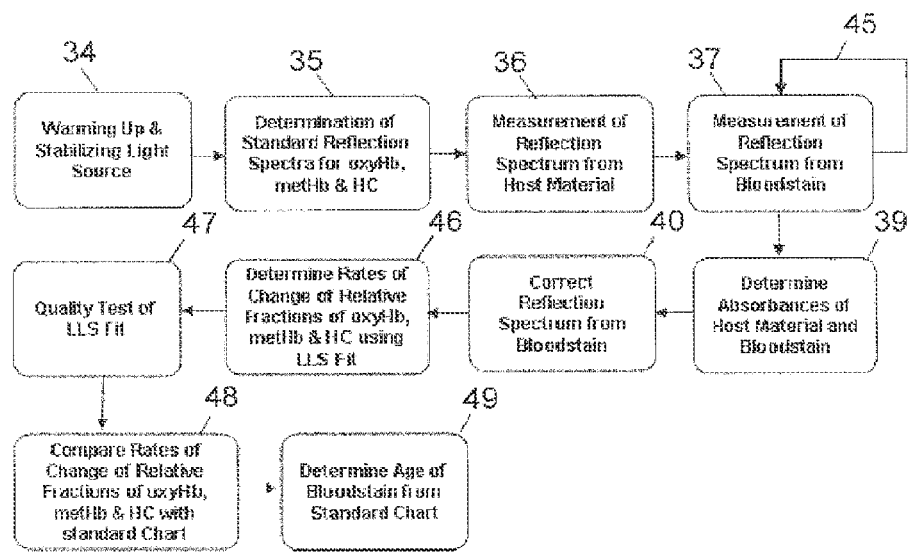
FIG. 12 is a schematic flowchart of a second process for determining the time at which blood was first exposed to air.

A second embodiment of the process described above is shown schematically in FIG. 12. In this case, the steps of warming up the lamp (34), determining the standard spectra for $HbO_2$, met-Hb and HC (35), measuring the reflection spectrum for the host material (36) and measuring the reflectance spectrum for the bloodstain (37) are the same as in the process described above. The latter measurement of the spectrum of the bloodstain (which may be measured at different positions on the bloodstain) is, however, then repeated several or many times over the course of minutes, hours or even days, as is indicated by the arrow 45. If the measurements are taken at different positions on the bloodstain, then the measurements at different times will, of course, be taken at the same corresponding positions. The measurements are repeated at different times in order to determine the reaction rate, i.e. the change in the concentration of each of the components of haemoglobin. Thus, in this case, rather than determining the concentrations of each of the components, the rates of change of the concentrations are determined (46) after the absorbances of the host material and the bloodstain have been determined (39) and the reflectance spectra have been corrected (40), as described above. Again, the determination of the rates of change of the concentrations is carried out using a LLS fit and a quality test of the fit is carried out (47). Thereafter, the rates of change of the concentrations, are compared (48) to the rates of change of concentrations of $HbO_2$, met-Hb and HC, i.e. the slopes of the lines in the graph of FIGS. 10*a,b*. The position where the sum of the differences is at a minimum is considered to be the best match and the age of the bloodstain is determined (49).

Figure 13:
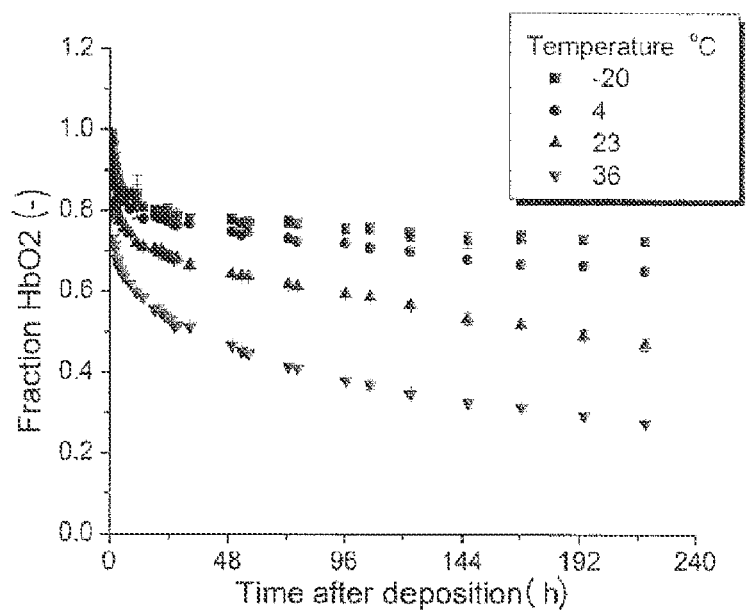
FIG. 13 is a graph showing experimental data of how the relative concentration of $HbO_2$ in a bloodstain changes over time at different temperatures.
Figure 14:
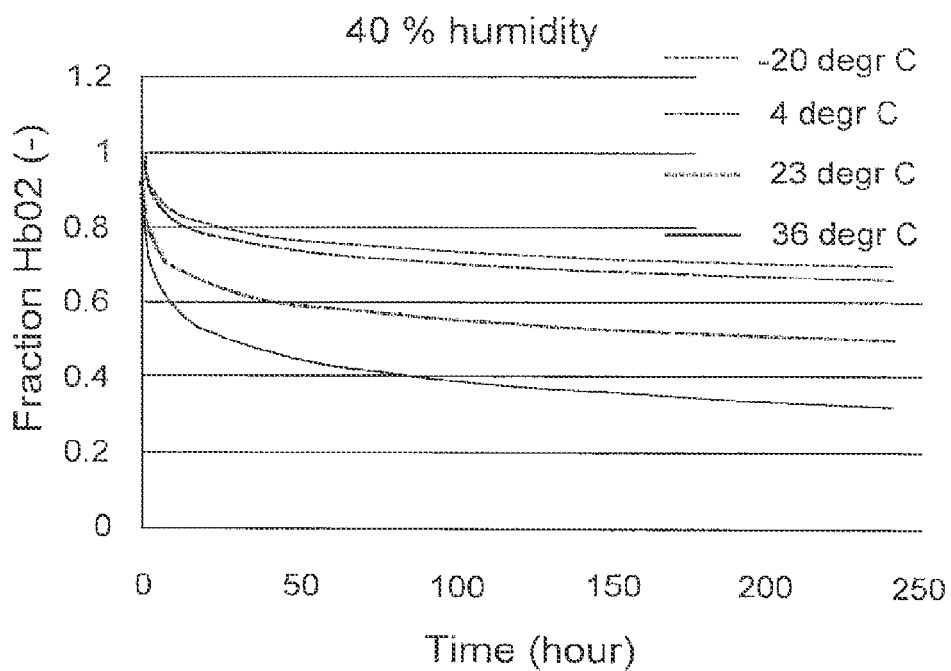
FIG. 14 is a line graph generated from the graph of FIG. 13 showing how the relative concentration of $HbO_2$ in a bloodstain changes over time at different temperatures.

As mentioned above with respect to FIGS. 10*a,b* the amount of $HbO_2$ decreases over time, because of the oxidation into met-Hb. However, it will be appreciated that the rate of the reaction can vary depending on environmental conditions, with a number of environmental factors, for example, ambient temperature, humidity, thermal conductivity of a substrate on which the body or body sample is located, absorption by a substrate on which the body or body sample is located and/or other factors affecting the rate. Thus, it is envisaged that "standard" graphs can be constructed for a number of different combinations of environmental factors, for different typical environmental conditions. For example, there may be several possible "standard" graphs of the amounts of the fractions, for different environments, each graph being a combination of the effects of different environmental factors for a particular "standard" environment, such as outdoors day or night, air conditioned indoors, non-air conditioned indoors day or night, etc. These "standard" graphs can be determined experimentally, for example, as shown in FIG. 13, which shows the experimental results from controlled experiments for the $HbO_2$ fraction at 40% humidity at ambient temperatures of −20° C., 4° C., 23° C. and 36° C. As can be seen, as the ambient temperature increases, the amount of $HbO_2$ present decreases more rapidly over time to a lower amount than at lower ambient temperatures. Such experimental graphs can be used to produce "standard graphs", by providing best fit lines to the experimental data, as shown in FIG. 14.

Figures 15, 16:
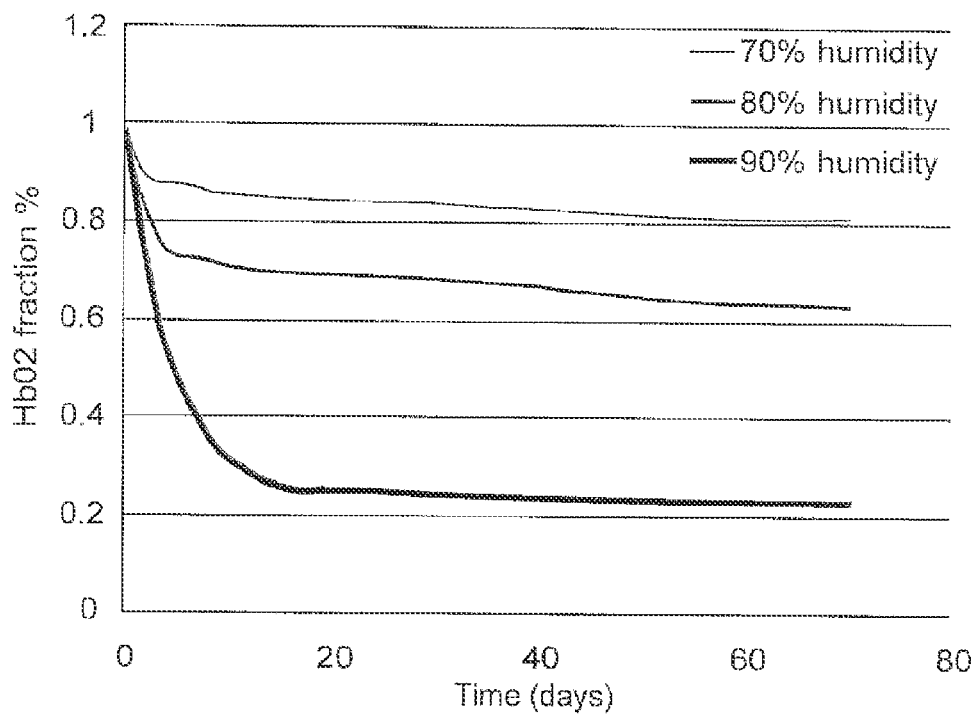
FIG. 15 is a graph showing how the relative concentrations of $HbO_2$ in a bloodstain changes over time at different humidities.
FIG. 16 is a table showing different values for equation parameters equivalent to the lines in the graph of FIG. 14.

Similarly, FIG. 15 shows how ambient humidity affects the decrease in the amount of $HbO_2$ present. The graph shows schematically the rates of decrease of the amount of $HbO_2$ present at ambient humidities of 70%, 80% and 90% humidity. As can be seen, as the ambient humidity decreases, the amount of $HbO_2$ present decreases more rapidly over time to a lower amount than at higher ambient humidities. Similar graphs can be constructed for other environmental factors, such as thermal conductivity of a substrate on which the body or body sample is located, absorption by a substrate on which the body or body sample is located and/or other factors affecting the rate, as well as graphs showing the amounts of the other components over time for the various environmental factors.

In order to carry out the comparison of the measured $HbO_2$, met-Hb and HC fractions to the "standard" graph therefore, a better estimate can be obtained by first choosing the best "standard" graph based on an estimate of the environment where the sample was found at the estimated time that the bloodstain originated. By thus choosing the most likely "standard" graph for that environment, a better estimate of the age of the bloodstain can be achieved.

Of course, it will be appreciated, that each of the graphs can be considered to have an equation associated with it, with different parameters for the rates of change of the component fractions depending on the particular environmental factors. For example, for the graph of FIG. 14, the various experimentally derived "standard" lines shown can be "converted" into an equation of the form:

$$\text{Fraction } HbO_2 = 1 - A \cdot \ln(\text{time} \cdot B)$$

where the parameters A and B take different values to provide the appropriate shape of the line at different temperatures. Of course, different "standard" graphs for different environmental factors may have different equations, not just different values of parameters A and B. Nevertheless, it will be apparent that, once appropriate experimental data has been gathered for the fractions of the components for different combinations of environmental factors, corresponding to different environmental conditions, then appropriate equations can be determined for each such graph.

These equations with different parameters can be stored in a database together with particular environment scenarios, each being associated with different set values of the various parameters. Thus, for example, an outdoor nighttime winter environment may have associated with it a lower temperature and a higher humidity than an outdoor daytime summer environment. It will be appreciated that many different such environmental scenarios can be stored, together with associated different values of the parameters of the equations, so that for any particular chosen environmental scenario, a particular set of associated values of the various parameters can be found from the database in order to determine the equation that produces the "standard" graph for that particular component fraction in that environment. FIG. 16, shows a table of various values of the parameters A and B for the equation:

$$\text{Fraction } HbO_2 = 1 - A \cdot \ln(\text{time} \cdot B)$$

for the fraction of $HbO_2$ for the graph shown in FIG. 14. The database would normally be stored in computer memory, coupled to a computer processor. As can be seen, the database can include particular examples of environmental conditions, so that, if a particular environmental condition is chosen by a user on the computer, using a computer user interface, the particular environmental factors and the values of the parameters corresponding to that chosen environmental condition, are automatically read by the computer processor from the database and, if desired, inserted into the appropriate equation, with the "standard" graph then being generated from that equation by the computer. The measured values can then be compared to that graph, either visually, using the graph itself, or by analyzing the measured amounts by the computer processor to compare them to the generated equation. For example, if a bloodstain is found outside in summer and it is estimated that it was outside all night, then the Outside Summer Night environment may be chosen. This equates to a temperature of 4° C. and a humidity of 40%, and the computer would then find from the database that A=0.0498 and b=3.8507 and generate the "standard" graph. If the measured $HbO_2$ fraction is 0.7, then it can be determined, either visually from the generated "standard" graph, or by the computer from the equation without the need for generating the "standard" graph, that the estimated age will be 107 hours.

Figure 17:
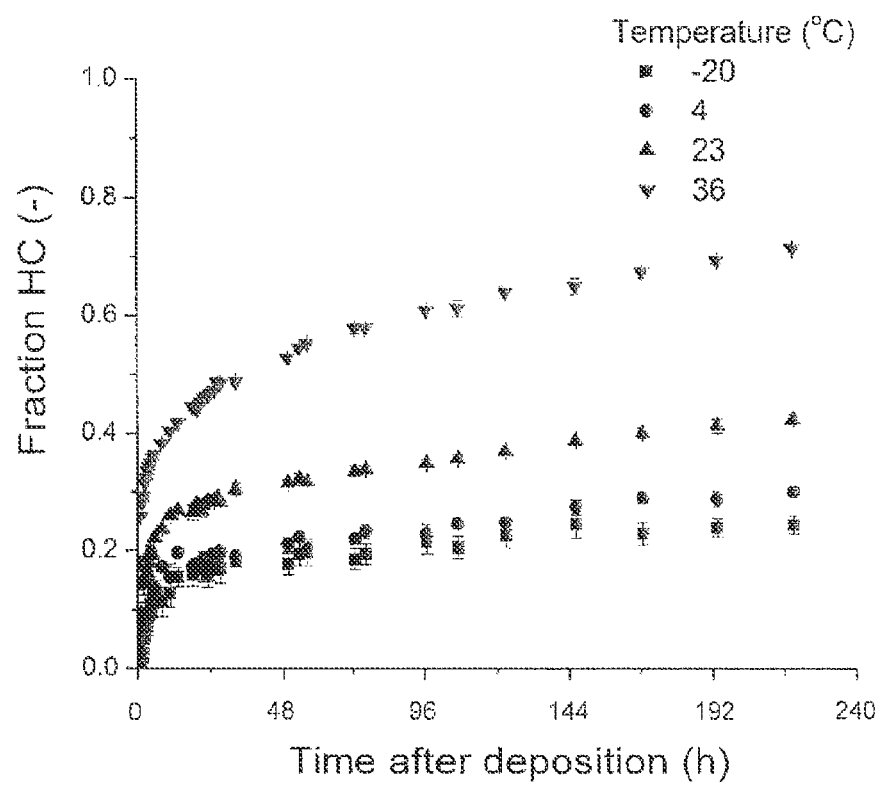
FIG. 17 is a graph showing experimental data of how the relative concentration of HC in a bloodstain changes over time at different temperatures.

Of course, it will be appreciated that such an analysis could, in fact, be undertaken for a number of differing environmental scenarios to find the best fit and/or for different component fractions, as described above. For example, FIG. 17 shows the experimentally determined graph for the HC component at a humidity of 40% for the same temperatures as those for which the $HbO_2$ fraction was determined. Thus, the measured HC component could also be compared to a "standard" graph and the age determined from that, thus enabling a more accurate overall age determination to be made.

It will be appreciated that although only a few particular embodiments of the invention has been described in detail, various modifications and improvements can be made by a person skilled in the art without departing from the scope of the present invention.

For example, when a sample such as a blood stain is deposited on a dark or coloured background that absorbs much of the visible light then reflectance spectroscopy can have shortcomings for the identification and age estimation of the sample. The inventors have found that near infra-red reflectance spectroscopy can distinguish blood samples from other substances on white and coloured backgrounds.

Figure 18:
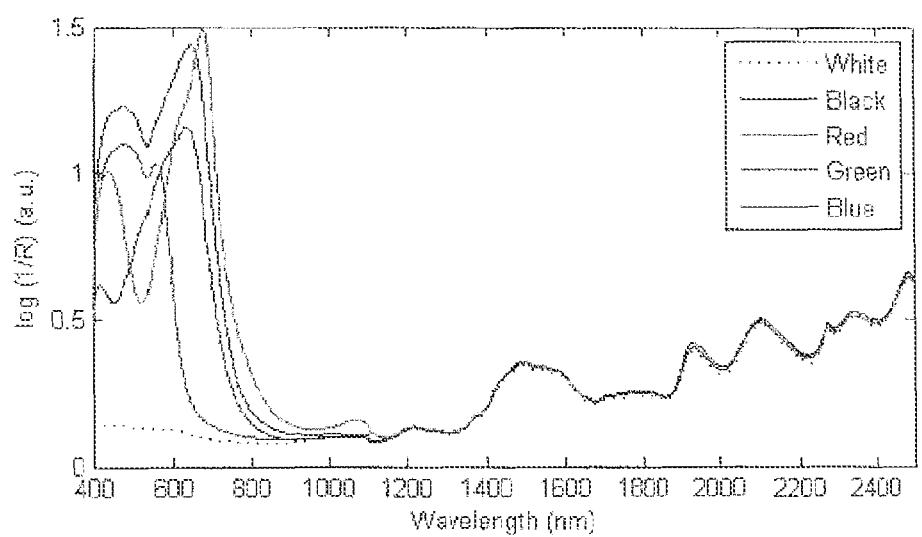
FIG. 18 is a graph of white and coloured cotton t-shirts background spectra in the near infrared part of the spectrum.

FIG. 18 shows white and coloured cotton t-shirt background spectra in the infrared range of the spectrum. For ease of comparison with literature data, the reflectance spectra is transformed to apparent absorbance spectra (log 1/reflectance or log 1/R). We can see that coloured cotton only differs in the visible part of the spectrum less than 850 nm but it the near infrared part of the spectrum all cotton colours have the same spectral features.

Blood was drawn from two healthy female volunteers and deposited on several backgrounds; brown cork and white, back, red, green and blue cotton. Next to three blood samples on each background, a reference sample of each plain background was created. Between measurements, all samples were stored in a laboratory with a stable room temperature and humidity.

It is known that variation between individual log(1/R) spectra is not only caused by the chemical composition of the sample, but also by different particle sizes, non-uniform light scattering and variable spectral path lengths. To minimize the spectral variation caused by non-chemical properties, several preprocessing methods (each described below) were applied to the log(1/R) spectra.

| Preprocessing method | Description |
| --- | --- |
| Offset correction | Each spectrum is corrected by subtracting either its value at one wavelength or the mean value in a selected range. |
| Multiplicative Scatter Correction (MSC) | Each spectrum is shifted and rotated so that it fits as closely as possible to the mean spectrum of the data. |
| Standard Normal Variate transformation (SNV) | The mean of each spectrum is subtracted, followed by division of the spectrum by its standard deviation. |
| First derivative | Differentiation by using the Savitsky-Golay algorithm. |
| Second derivative | Differentiation by using the Savitsky-Golay algorithm. |

For blood stain identification, a preferred preprocessing method would remove spectral variation between blood samples while conserving spectral variation between blood samples and other substances. We calculated the coefficient of variation at each wavelength for all preprocessed spectra, to determine which (preprocessed) spectral features are stable and thus suitable to use for the identification of blood stains.

For the purpose of age estimation, a preferred preprocessing method would remove spectral variation between blood samples of the same age while conserving spectral variation between blood samples of different ages. We calculated the coefficient of determination $R^2$ between the logarithm of the age and all preprocessed spectra at each wavelength. All coefficients of determination were compared to choose the most useful preprocessing method and to see which spectral changes correlate highly with the age of blood stains.

Partial Least Squares regression (PLS) was used to create a model predicting the age of blood stains based on the log(1/R) spectra. PLS is a useful statistical tool for the analysis of spectroscopic data, as it can handle datasets in which there are more variables than observations, and the data may contain highly correlated predictor variables. PLS makes linear combinations of the original predictor variables to construct new predictor variables, which are the most relevant for predicting the age. All ages of blood stains on white cotton and brown cork were estimated using a leave-one-out cross-validation (CV) and the root mean squared errors of cross validation (RMSECV) were calculated. Results were compared for models using the visible (Vis) wavelength range, the near infrared (NIR) range and a combination of these (Vis-NIR).

The log(1/R) spectra of the differently coloured cotton backgrounds were compared visually. Based on this comparison, a wavelength region was chosen in which the colour of the background did not influence the spectra. This region was used to estimate the age of blood stains on coloured backgrounds, using a PLS model which was trained with the blood stains on the other backgrounds. Finally, the root mean squared errors of prediction (RMSEP) were calculated for all colours.

Figure 19:
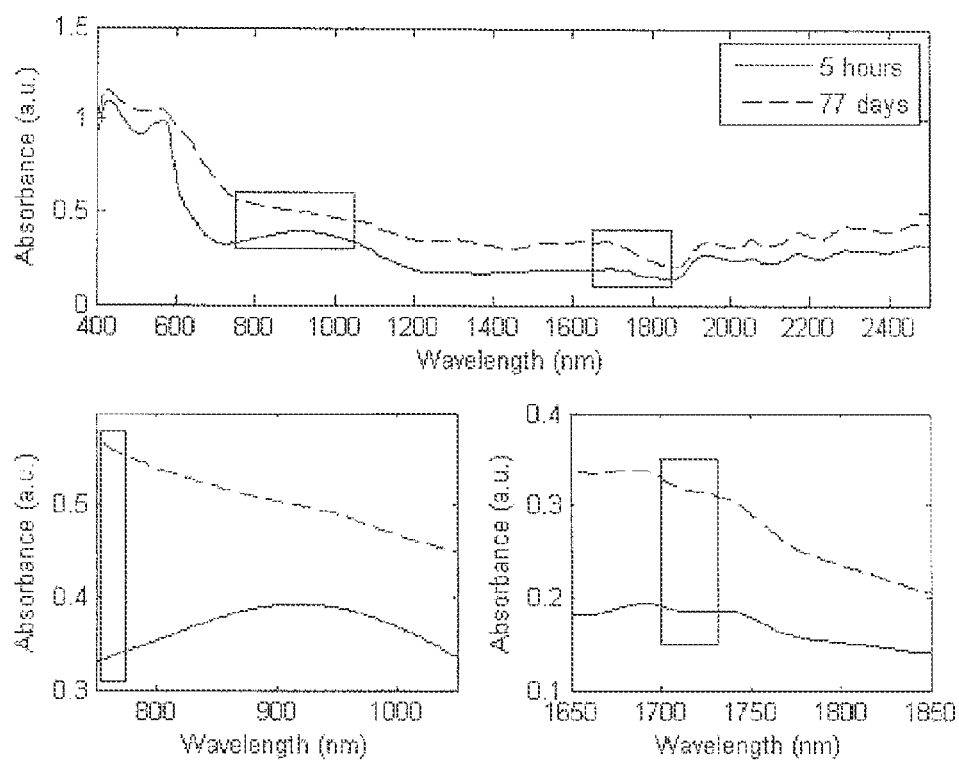
FIG. 19 is a graph of first derivative spectra of blood stains of 5 hours and 77 days old.

The highest coefficients of determination $R^2$ were found when using the first derivative spectra. In two regions of the first derivative spectra $R^2$ was higher than 0.975. These regions are depicted in FIG. 19. The first region (from 754 to 774 nm) was near a broad absorption peak of oxyhemoglobin. The second region (from 1700 to 1732 nm) was between two typical absorption peaks (at 1690 and 1740 nm) known to be present in the spectra of haemoglobin, albumin, globulin, and glucose. FIG. 19 shows absorbance spectra of fresh (5 hours, solid line) and old (77 days, hatched line) blood stains corrected for a cotton background.

Figure 20:
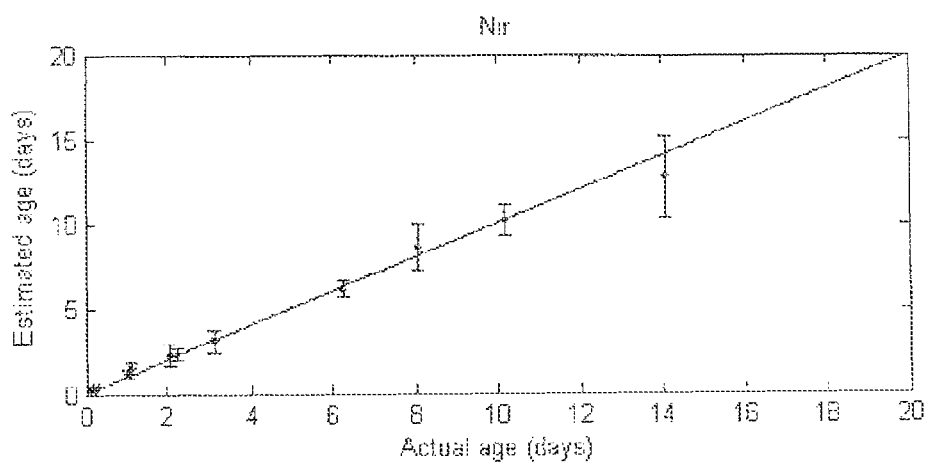
FIG. 20 is an age estimation of back cotton using the predetermined regions in the near infrared part of the spectrum.

FIG. 20 shows an age estimation on black cotton using the predetermined regions in the near infrared part of the spectrum. This model can be used to predict the age of the blood stains on the remaining background. The root mean squared error of prediction (RMSEP) was 8.9%.

The invention claimed is:

1. A method of dating a body sample comprising:
    taking at least one spectroscopic measurement of the sample, the measurement including at least two predetermined positions in a spectrum, the positions having spectral characteristics corresponding to at least two predetermined substances present in the sample that have a time varying relationship with respect to each other;
    wherein the method comprises determining a measured relative concentration of each of the predetermined substances present in the sample from the spectroscopic measurement;
    comparing the measured relative concentrations of said at least two predetermined substances with a known variation of relative concentrations of the at least two predetermined substances over time; and
    providing an indication of age of the sample based on a correlation criterion between the measured relative concentrations and the known variation of the relative concentrations.

2. The method of dating a body sample according to claim 1, wherein said sample is a body fluid.

3. The method of dating a body sample according to claim 2, wherein said body fluid is blood.

4. The method of dating a body sample according to claim 3, wherein the predetermined substances comprise at least two of oxy-haemoglobin, met-haemoglobin and haemichrome.

5. The method of dating a body sample according to claim 4, wherein the measurement includes at least three predetermined positions in the spectrum, the positions having spectral characteristics corresponding to at least three predetermined substances, said three predetermined substances comprising oxy-haemoglobin, met-haemoglobin and haemichrome.

6. The method of dating a body sample according to claim 1, wherein the spectroscopic measurement comprises reflectance, Raman and/or a fluorescence spectroscopic measurement.

7. A method of dating a body sample, comprising:
    taking at least two spectroscopic measurements of the sample at different times, the measurements including at least two predetermined positions in a spectrum, said positions having spectral characteristics corresponding to at least two predetermined substances present in the sample that have a time varying relationship with respect to each other;
    wherein the method comprises determining a measurement of change in a relative concentration of each of said predetermined substances present in the sample with respect to each other from the spectroscopic measurements;

comparing the measurements of change in the relative concentration of each of said predetermined substances with a known variation of the change in the relative concentration of the predetermined substances over time; and providing an indication of age of the sample based on a correlation criterion between the measurements of changes in the relative concentration and the known variation of the change in the relative concentrations.

8. The method of dating a body sample according to claim 7, the method further comprising:

taking at least one spectroscopic measurement of the sample, the measurement including at least two predetermined positions in a spectrum, the positions having spectral characteristics corresponding to at least two predetermined substances present in the sample that have a time varying relationship with respect to each other;

determining a measured relative concentration of each of the predetermined substances present in the sample from the spectroscopic measurement; comparing the measured relative concentrations of said at least two predetermined substances with a known variation of relative concentrations of the at least two predetermined substances over time; and providing an indication of age of the sample based on a correlation criterion between the measured relative concentrations and the known variation of the relative concentrations, so as to provide an indication of age of the sample.

9. A method of dating a blood sample, said method comprising:

measuring one or more time-varying parameters of the blood sample, the time-varying parameter having a rate of time variance that changes according to at least one environmental factor;

providing a database of rates of time variance of the time-varying parameter for the at least one environmental factor;

estimating the at least one environmental factor for a particular environment where the blood sample was located prior to measuring the one or more time-varying parameters of the blood sample; and determining an estimate of age of the blood sample utilising one of or each of the measured time-varying parameter and the rate of time variance for a specific time-varying parameters for the estimated at least one environmental factor, wherein said specific time-varying parameters comprises a relative concentration of at least two of:

concentration of oxy-haemoglobin;

concentration of met-haemoglobin; and concentration of haemichrome.

10. The method of dating a blood sample according to claim 9, wherein said time-varying parameter comprises temperature.

11. The method of dating a blood sample according to claim 9, wherein the environmental factor comprises at least one of:

ambient temperature;

ambient humidity;

thermal conductivity of a substrate on which the blood sample is located; and absorption by a substrate on which the blood sample is located.

12. An apparatus for dating a body sample comprising:

a device for taking at least one spectroscopic measurement of the sample, said measurement including at least two predetermined positions in a spectrum, the positions having spectral characteristics corresponding to at least two predetermined substances present in the sample that have a time varying relationship with each other; and wherein the apparatus comprises a processing device for determining a measured relative concentration of each of the predetermined substances present in the sample from the spectroscopic measurement, comparing the measured relative concentrations of said at least two predetermined substances with a known variation of the relative concentrations of said at least two predetermined substances over time, and determining a correlation coefficient between the measured relative concentrations and the known variation of the relative concentrations so as to provide an indication of age of the sample on the basis of the correlation coefficient.

13. The apparatus for dating a body sample according to claim 12, wherein said sample is a body fluid.

14. The apparatus for dating a body sample according to claim 13, wherein said body fluid is blood.

15. The apparatus for dating a body sample according to claim 14, wherein the predetermined substances comprise at least two of oxy-haemoglobin, met-haemoglobin and haemichrome.

16. The apparatus for dating a body sample according to claim 15, wherein the measurement includes at least three predetermined positions in the spectrum, the positions having spectral characteristics corresponding to at least three predetermined substances, said three predetermined substances comprising oxy-haemoglobin, met-haemoglobin and haemichrome.

17. The apparatus for dating a body sample according to claim 12, wherein the spectroscopic measurement comprises reflectance, Raman and/or fluorescence spectroscopic measurement.

18. An apparatus for dating a body sample comprising:

a device for taking at least two spectroscopic measurements of the sample at different times, the measurements including at least two predetermined positions in a spectrum, the positions having spectral characteristics corresponding to at least two predetermined substances present in the sample that have a time varying relationship with each other; and wherein the apparatus comprises a processing device for determining a measurement of change in the relative concentration of each of said predetermined substances present in the sample from the spectroscopic measurements, comparing the measurements of change in the relative concentration of each of the predetermined substances with a known variation of the changes in the relative concentrations of the predetermined substances over time, and determining a correlation coefficient between the measurements of changes in the relative concentration and the known variation of the changes in the relative concentrations so as to provide an indication of age of the sample on the basis of the correlation coefficient.

19. The apparatus for dating a body sample according to claim 18, wherein, the processing device further determines a measured relative concentration of each of the predetermined substances present in the sample from the spectroscopic measurement, compares the measured relative concentrations of the at least two predetermined substances with a known variation of the relative concentrations of the at least two predetermined substances over time, and determines a correlation coefficient between the measured relative concentrations and the known variation of the relative concentrations so as to provide an indication of age of the sample on the basis of the correlation coefficient.

20. An apparatus for dating a body or body sample, comprising:
- a device for taking at least one measurement of at least one time-varying parameter of the body or body sample, the time-varying parameter having a rate of time variance that changes according to at least one environmental factor; and
- a processing device for obtaining a rate of time variance of said time-varying parameter for the at least one environmental factor, for a particular environment where the body or body sample was located prior to said at least one measurement being made, from a database of different rates of time variance of the time-varying parameter for different environments, and determining an estimate of age of the body or body sample utilising said at least one measurement of the or each time-varying parameter and the rate of time variance for a specific time-varying parameter, wherein said specific time-varying parameter comprises a relative concentration of at least two of:
- concentration of oxy-haemoglobin;
- concentration of met-haemoglobin; and
- concentration of haemichrome.

21. The apparatus for dating a body or body sample according to claim 20, wherein said time-varying parameter comprises temperature.

22. The apparatus for dating a body or body sample according to claim 20, wherein the environmental factor comprises at least one of:
- ambient temperature;
- ambient humidity;
- thermal conductivity of a substrate on which the body or body sample is located; and
- absorption by a substrate on which the body or body sample is located.

* * * * *